US009000052B2

(12) United States Patent
Berthier et al.

(10) Patent No.: US 9,000,052 B2
(45) Date of Patent: Apr. 7, 2015

(54) PERFUMING COMPOSITIONS AND USES THEREOF

(75) Inventors: Damien Berthier, Geneva (CH); Sébastien Lecommandoux, Canejan (FR); Isabelle Schmidt, Yverdon-les-Bains (CH); Christophe Schatz, Ayguemorte les Graves (FR)

(73) Assignee: Firmenich SA, Geneva (CH)

( * ) Notice: Subject to any disclaimer, the term of this patent is extended or adjusted under 35 U.S.C. 154(b) by 335 days.

(21) Appl. No.: 13/123,627

(22) PCT Filed: Oct. 19, 2009

(86) PCT No.: PCT/IB2009/054584
§ 371 (c)(1),
(2), (4) Date: Apr. 11, 2011

(87) PCT Pub. No.: WO2010/046832
PCT Pub. Date: Apr. 29, 2010

(65) Prior Publication Data
US 2011/0195037 A1   Aug. 11, 2011

(30) Foreign Application Priority Data

Oct. 21, 2008  (WO) .................. PCT/IB2008/054337
Nov. 7, 2008  (EP) ..................................... 08168672
Dec. 23, 2008  (WO) .................. PCT/IB2008/055502

(51) Int. Cl.
*A61K 8/34* (2006.01)
*A61K 8/893* (2006.01)
*A61Q 13/00* (2006.01)
*A61K 8/90* (2006.01)
*A61Q 15/00* (2006.01)
*A61Q 19/00* (2006.01)

(52) U.S. Cl.
CPC . *A61Q 13/00* (2013.01); *A61K 8/34* (2013.01); *A61K 8/893* (2013.01); *A61K 8/90* (2013.01); *A61K 2800/594* (2013.01); *A61Q 15/00* (2013.01); *A61Q 19/002* (2013.01)

(58) Field of Classification Search
None
See application file for complete search history.

(56) References Cited

U.S. PATENT DOCUMENTS

| | | | | |
|---|---|---|---|---|
| 5,066,485 A | 11/1991 | Brieva et al. | | 424/63 |
| 5,649,979 A | 7/1997 | Paget et al. | | 8/137 |
| 5,840,280 A | 11/1998 | Faryniarz et al. | | 424/47 |
| 5,853,700 A | 12/1998 | Gormley et al. | | 424/47 |
| 6,133,228 A | 10/2000 | Pika et al. | | 512/21 |
| 6,139,851 A | 10/2000 | Omura et al. | | 424/401 |
| 6,218,355 B1 | 4/2001 | Herrmann | | 512/27 |
| 6,319,489 B1 | 11/2001 | Ashton et al. | | 424/47 |
| 6,369,026 B1 | 4/2002 | Pika et al. | | 512/21 |
| 6,635,262 B2 | 10/2003 | Jourdan et al. | | 424/400 |
| 6,677,297 B2 | 1/2004 | Frerot | | 512/20 |
| 7,723,286 B2 | 5/2010 | Fehr et al. | | 512/8 |
| 2001/0041771 A1 | 11/2001 | Kondo et al. | | 525/100 |
| 2002/0016382 A1 | 2/2002 | Kondo et al. | | 523/102 |
| 2002/0035229 A1 | 3/2002 | Kondo et al. | | 528/10 |
| 2003/0012758 A1* | 1/2003 | Jourdan et al. | | 424/70.11 |
| 2004/0102357 A1 | 5/2004 | Smith et al. | | 512/3 |
| 2009/0053301 A1 | 2/2009 | Lin et al. | | 424/450 |
| 2009/0181878 A1 | 7/2009 | Fehr et al. | | 512/7 |
| 2010/0098650 A1 | 4/2010 | Herrmann et al. | | 424/65 |

FOREIGN PATENT DOCUMENTS

| | | |
|---|---|---|
| DE | 30 03 494 A1 | 8/1980 |
| DE | 10 2006 024 397 B3 | 10/2007 |
| EP | 0 875 235 A2 | 11/1998 |
| EP | 0 936 211 A2 | 8/1999 |
| EP | 0 971 021 A1 | 1/2000 |
| EP | 1 138 315 A1 | 10/2001 |
| GB | 2 041 964 A | 9/1980 |
| JP | 54-73136 A | 6/1979 |
| JP | 08-003582 A | 1/1996 |
| JP | 2006-342096 A | 12/2006 |
| RU | 2 234 913 C1 | 8/2004 |
| WO | WO 95/04809 A1 | 2/1995 |
| WO | WO 95/08976 A1 | 4/1995 |
| WO | WO 98/47477 A1 | 10/1998 |
| WO | WO 99/60990 A1 | 12/1999 |
| WO | WO 01/28980 A1 | 4/2001 |
| WO | WO 03/049666 A2 | 6/2003 |
| WO | WO 03/090706 A1 | 11/2003 |
| WO | WO 2007/100416 A1 | 9/2007 |
| WO | WO 2008/093272 A2 | 8/2008 |

OTHER PUBLICATIONS

International Search Report and Written Opinion mailed Apr. 19, 2010, Application No. PCT/IB2009/054584 filed Oct. 19, 2009.
Database WPI Week 200709, Thomson Scientific, London, GB; AN 2007-086839, XP002570077 & JP 2006-342096 A, Dec. 21, 2006, abstract.
Database WPI Week 197929, Thomson Scientific, London, GB; AN 1979-53715B, XP002570078 & JP 54-073136 A, Jun. 12, 1979, abstract.

* cited by examiner

*Primary Examiner* — Michael B Pallay
(74) *Attorney, Agent, or Firm* — Winston & Strawn LLP

(57) ABSTRACT

A perfuming composition capable of prolonging the release of a perfuming component into the surrounding environment when applied on a surface. This composition utilizes hydrophobic block copolymers in the presence of high amounts of ethanol. The invention also relates to consumer articles containing such compositions. It finally provides methods for the perfuming of a surface and a method for increasing the long-lastingness of a perfuming component using these compositions.

16 Claims, 9 Drawing Sheets

PERFUMING COMPOSITIONS AND USES THEREOF

This application is a 371 filing of International Patent Application PCT/IB2009/054584 filed Oct. 19, 2009.

TECHNICAL FIELD

The present invention relates to the field of perfumery. More particularly, it provides a perfuming composition capable of prolonging the release of a perfuming component into the surrounding environment when applied on a surface. The composition comprises hydrophobic block copolymers in the presence of high amounts of ethanol. The invention also relates to consumer articles containing such compositions. It finally provides methods for the perfuming of a surface and a method for increasing the long-lastingness of a perfuming component using these compositions.

PRIOR ART

In the perfumery industry there is a constant need to find new technologies for prolonging the perception of perfumes. Indeed, perfuming ingredients are usually volatile compounds which evaporate quickly, the perfume intensity decreasing with time. It is therefore desirable to delay the evaporation of ingredients in perfuming compositions. Such compositions being usually in the form of solutions with ethanol as solvent, it is therefore desirable to provide perfuming compositions comprising high amounts of ethanol and having a long-lasting perfume intensity.

Amphiphilic copolymers are used in perfuming compositions for the retention of perfuming ingredients. The retention ability of these compositions is a consequence of the ability of the polymers they contain to form micelles or vesicles. However, these polymers lose their ability to form these types of aggregates in the presence of high amounts of ethanol, therefore reducing the efficiency of the compositions to retain perfuming ingredients or prolong their perception. Since ethanol is the current solvent for perfumes, it would be useful to be able to provide perfuming compositions capable of releasing perfuming ingredients more efficiently in the presence of high amounts of ethanol.

To the best of our knowledge, the perfuming compositions of the invention are not known from the prior art. In particular, there is no report of the use of the hydrophobic block copolymers used in the perfuming compositions of the invention together with high amounts of ethanol.

WO 03/090706 describes a fragrance releasing complex based on entrapment material comprising polymers. These polymers are amphiphilic and are active only in low amounts of ethanol. This document therefore does not address the problem of the retention of perfuming ingredients in high amounts of ethanol.

WO 2007/100416 describes compositions comprising silicone vesicles containing a hydrophobic active and up to 50% of ethanol. Suitable silicones are organopolysiloxanes having at least one hydrophilic substituent group. The hydrophilic group can be selected among different chemical moieties that are commonly used in combination with various hydrophobic chemical moieties to create surfactant structures or molecules having surface active behaviour. Therefore the compositions of the invention differ from the compositions of this prior art document in that they comprise at least one polymeric material which is hydrophobic silicones, and this particular choice of polymeric material presents the advantage of being capable of efficiently retaining perfuming ingredients even in the presence of concentration of ethanol of up to 90%.

The present invention brings a novel and advantageous solution to the problem of providing an efficient system for increasing the long-lastingness of perfuming component from compositions comprising high amounts of ethanol, once applied on surfaces.

DESCRIPTION OF THE INVENTION

The present inventors have surprisingly established that perfumery ingredients can be efficiently released from perfuming compositions comprising a specific class of hydrophobic block copolymers and high amounts of ethanol.

Therefore, the present invention provides a perfuming composition comprising
a) at least one hydrophobic polymeric material which is water insoluble and which is formed of
   i) at least one ethanol-compatible block;
   ii) at least one ethanol-incompatible block comprising a poly(dimethylsiloxane) or a derivative thereof;
b) from 25 to 90% of ethanol;
c) water; and
d) at least one perfuming component.

According to a preferred embodiment, the perfuming composition consists of
a) at least one hydrophobic polymeric material which is water insoluble and which is formed of
   i) at least one ethanol-compatible block;
   ii) at least one ethanol-incompatible block comprising a poly(dimethylsiloxane) or a derivative thereof;
b) from 25 to 90% of ethanol;
c) water; and
d) at least one perfuming component.

By "consists" it is meant here that the composition consists essentially of the recited components but may contain other ingredients that do not have an impact on the release of the perfume component.

The specific class of hydrophobic polymeric materials used in the compositions of the invention must be water insoluble.

A component is considered as being insoluble in a given solvent at a defined concentration, temperature, pH, ionic strength and in the presence or not of other solutes, when the component phase separates from the solvent phase. Phase separation may be easily observed by knowledgeable practitioners in the domain, using methods amongst which are visual, microscopic or interferential. In particular, when the component is a solid, a precipitate can be observed.

According to a particular embodiment of the invention, a polymer is "insoluble in water" if it cannot be solubilised in water, without phase separation, at a concentration of at least 0.3% by weight relative to the total weight of the solution, and a temperature range between room temperature and skin temperature, meaning typically between 20° C. and 37° C., and more particularly in the range of 25 to 32° C. To the contrary, a polymer is considered as "soluble in water" if it can be solubilised in water at concentrations of at least 0.3% by weight relative to the total weight of the solution at the temperatures indicated above, and preferably both at 32 and 25° C.

The hydrophobic polymeric material must comprise at least one ethanol-compatible block and at least one ethanol-incompatible block. As an "ethanol-compatible block" it is intended to mean here, for the purpose of the present invention, a polymer that can be solubilised in ethanol without phase separation at a concentration of at least 0.3% by weight relative to the total weight of the solution. As an "ethanol-incompatible block" we mean here, a polymer which cannot be solubilised in ethanol without phase separation at a concentration of at least 0.3% by weight relative to the total weight of the solution.

Both the ethanol incompatible block and the ethanol compatible block are hydrophobic (i.e. are insoluble in water).

Preferred ethanol compatible blocks can be advantageously selected from the group consisting of poly(propylene glycol), poly(1,2-butylene glycol) and poly(1,4-butylene glycol). More preferably the ethanol compatible block is poly(propylene glycol) or poly(1,2-butylene glycol).

Preferably the polymer used in the perfuming compositions of the invention does not comprise any poly(ethylene glycol) block.

In a preferred embodiment of the invention, the ethanol-incompatible block consists of a poly(dimethylsiloxane).

Optimal perfume release performance can be obtained by selecting specific polymer parameters. For example, it is preferred that the hydrophobic polymeric material has a grafted structure with a poly(dimethylsiloxane) core. It is even more advantageous that hydrophobic ethanol-compatible blocks are linked as side chains to the poly(dimethylsiloxane) core. It is also preferred that the polymeric material comprises high amounts of poly(dimethylsiloxane), preferably more than 50% of its own weight.

The efficiency of the composition of the invention is further improved when the hydrophobic polymeric material has high molecular weight, preferably comprised between 300 and 100'000 g/mol, more preferably between 300 and 15'000 g/mol.

The perfuming compositions of the invention are capable of efficiently prolonging the perception of the perfuming component even when the hydrophobic polymeric material does not self-assemble in aggregates such as micelles or vesicles. Nevertheless, the retention is further improved when micelles or vesicles are formed. Typically, the size of these micelles or vesicles will not exceed 200 nm, so that the compositions are still transparent. The formation of micelles or vesicles is favoured when the polymeric material comprises a high proportion of ethanol incompatible block, for example when more than 50% by weight of the hydrophobic polymer consists of at least one ethanol incompatible block.

The at least one hydrophobic polymeric material can be present in the composition of the invention in an amount comprised between 0.1 and 30% by weight, relative to the total weight of the composition. More advantageously, it is present in an amount comprised between 0.1 and 10% by weight or even between 0.1 and 5% by weight, relative to the total weight of the composition.

The perfuming component present in the perfuming composition of the invention is defined here as a compound which is used in a perfuming preparation or composition to impart a hedonic effect. In other words such a perfuming component, in order to be considered as such, must be recognized by a person skilled in the art as being able to impart or modify in a positive, desirable or pleasant way the odor of a composition, article or surface on which it is applied, and not just as having an odor. Compounds capable of modifying the perception by a consumer of a compound as defined above are also considered as perfuming components.

Typically, the perfume component of the composition is a mixture of perfuming ingredients, possibly together with current perfume carriers.

The nature and type of the perfuming components that can be used in the perfuming compositions of the invention do not warrant a more detailed description here, which in any case would not be exhaustive, the skilled person being able to select them on the basis of its general knowledge, the intended use or application and the desired organoleptic effect. In general terms, these perfuming components belong to chemical classes as varied as alcohols, aldehydes, ketones, esters, ethers, acetates, nitriles, terpene hydrocarbons, nitrogenous or sulphurous heterocyclic compounds and essential oils, and said perfuming components can be of natural or synthetic origin. Many of these ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery.

It is also understood that the perfuming component may also comprise encapsulated perfuming ingredients or yet known release systems wherein the active ingredient is released as a result of a chemical or photochemical reaction, provided that such perfume component is used under the conditions of application onto surfaces which allow the release of the corresponding active perfuming component. Examples of such release systems are found for example in WO 95/04809, EP 0971021, WO 03/049666, EP 0936211, WO 99/60990, WO 01/28980, WO 08/093,272, WO 98/47477, US 2004/0102357, DE 30 03 494 and WO 95/08976.

The amount of perfuming component in the composition of the invention can vary in a wide range of values, depending on the desired intensity of fragrance perception. These compositions are advantageously characterized by the fact that they are able to contain high loads of perfume. Preferably, the amount of perfuming component is comprised between 0.2 and 30% by weight, more preferably between 5 and 15% by weight, relative to the total weight of the composition. Concentrations of around 10% by weight of perfuming component have provided excellent results.

According to a preferred embodiment of the invention, the weight ratio of hydrophobic polymeric material to perfuming component is comprised between 0.1:10 and 5:10, preferably between 0.1:10 and 1:10.

The compositions of the invention are preferably characterized by a high amount of ethanol, more preferably above 50% of the weight of the composition, preferably between 55 and 90% by weight and even more preferably between 60 and 90% by weight, relative to the total weight of the composition.

The concentration of water in the perfuming compositions of the invention is relatively low, typically comprised between 5 and 50% by weight, preferably between 5 and 15% by weight, relative to the total weight of the composition.

By "perfumery carrier" we mean here a material which is practically neutral from a perfumery point of view, i.e. which does not significantly alter the organoleptic properties of perfuming components. Said carrier may preferably be a liquid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

A perfume adjuvant such as an ingredient capable of imparting an-added benefit such as a color, a particular light resistance, chemical stability or anti-oxidant properties, etc. may also be present in the composition. A detailed description of the nature and type of adjuvant commonly used in perfuming bases cannot be exhaustive, but such ingredients are well known to a person skilled in the art and are typically used in concentrations of not more than 0.5%.

A perfuming composition according to any of the embodiments described above is a useful perfuming material, which can be advantageously used in all the fields of modern perfumery, such as fine perfumery or functional perfumery. Indeed, such compositions may be advantageously employed in fine or functional perfumery to achieve a more controlled deposition, and consequent release, of perfuming components.

For example, the compositions of the invention, owing to a capability to provide long-lastingness of odoriferous or odor impacting molecules perception, can be incorporated in any application requiring the long-lastingness of an odoriferous component as defined hereinabove and furthermore can impart a fragrance and a freshness to a treated surface which will last well beyond the treatment period, for example in laundry or body care applications, well beyond the surface rinsing and/or drying processes. Suitable application surfaces for the perfuming compositions of the invention are, in particular, skin and hair, but also textiles, hard surfaces such as glass windows, kitchen and bathroom surfaces.

Consequently, an article comprising:
a) at least one perfuming composition of the invention, as defined above; and
b) a consumer product base;
is also an object of the present invention, as is the use of such a composition for the treatment of a surface such as those above-mentioned.

For the sake of clarity, it has to be mentioned that, by "consumer product base" we mean here a consumer product base which is compatible with perfuming ingredients. In other words, a perfumed article according to the invention comprises the base functional formulation (typically having as a function to clean, emulsify, moisturize or soften the surface to which it is applied), as well as optional additional benefit agents, corresponding to a consumer product, e.g. a hair or body care product such as a shampoo or shower gel, a detergent or an air freshener, together with an olfactively effective amount of at least one perfuming composition according to the invention.

The nature and type of the constituents of the consumer product do not warrant a more detailed description here, which in any case would not be exhaustive, the skilled person being able to select them on the basis of its general knowledge and according to the nature and the desired effect of said product and its application.

In particular, the compositions of the invention are most advantageous for body care product use. They are much appreciated perfumes, i.e. fine fragrance products for perfuming the skin and hair. Preferred applications are a perfume, a cologne or body splash, an after-shave lotion, a perfumed soap, a shower or bath salt, mousse, cream, oil or gel, a body care product, a hair care product such as a shampoo, a deodorant or antiperspirant.

Examples of other suitable consumer product bases include hygiene products, air fresheners and cosmetic preparations.

The proportions in which the perfuming compositions of the invention can be incorporated into the various aforementioned articles or compositions vary within a wide range of values. These values are dependent upon the nature of the article or product into which they are to be incorporated and on the desired olfactory effect, as well as the nature of the perfuming components present in the composition.

For example, in fine fragrance products, the composition of the invention can be used in concentrations of up to 100%. In the other application types such as in body care and hair care products, the concentration of the perfuming composition of the invention is typically comprised between 1% and 20% by weight, more typically of up to 5% by weight, relative to the weight of the product.

Another object of the present invention relates to a method for the perfuming of a surface or to a method for intensifying or prolonging the diffusion effect of the characteristic fragrance of a perfuming component on a surface, characterized in that said surface is treated with a perfuming composition or a perfumed article containing the latter, as defined above, under conditions which are susceptible of allowing the release of said perfuming component, as defined above. Suitable surfaces for such treatment are, in particular hair and skin, but also textiles and hard surfaces.

The perfuming compositions according to the invention can be prepared by first dissolving the hydrophobic polymeric material in an ethanol-water mixture, the at least one perfuming component being in turn dissolved in the resulting solution.

EXAMPLES

Figure 1:
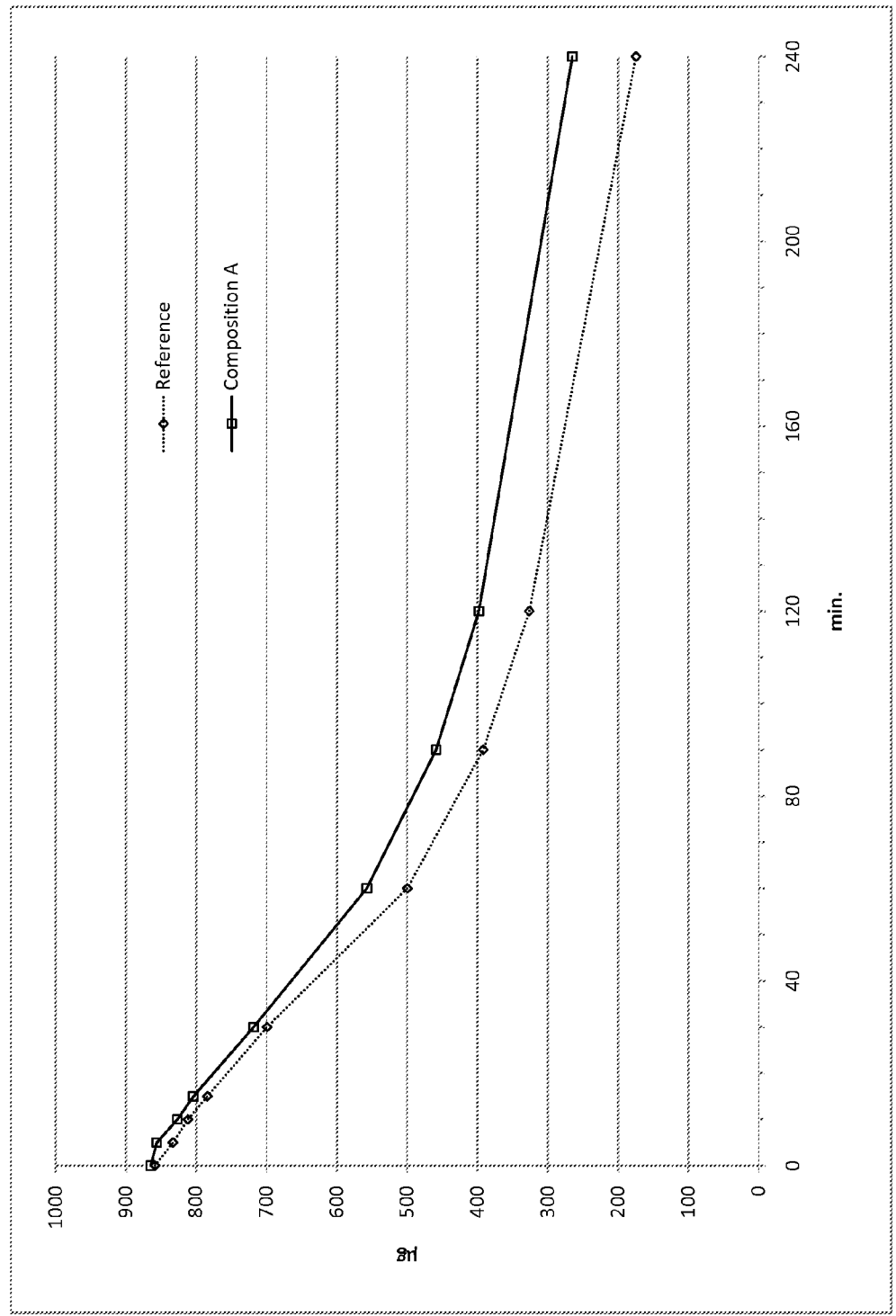
FIG. 1: This graph shows the disappearance of the perfume in Composition A and in the reference as a function of time.

The invention will now be described in further detail by way of the following examples, wherein the abbreviations have the usual meaning in the art. In all the evaluation tests described below, involving the use of panelists, the evaluation was carried out on a blind test, meaning that the panelists did not know the composition of the evaluated sample.

Example 1

Preparation of a Perfuming Composition According to the Invention

A perfume was prepared by admixing the following ingredients, in the amounts indicated.

TABLE 1

Perfume A

| Ingredients | Parts (by weight) |
| --- | --- |
| Ethyl Butyrate | 9.09 |
| Cis-3-hexenol | 9.09 |
| Ethyl 2-methyl-pentanoate[1] | 9.09 |
| (Z)-3-hexenyl acetate | 9.09 |
| Limonene | 9.09 |
| Dihydromyrcenol | 9.09 |
| 2,4-Dimethyl-3-cyclohexene-1-carbaldehyde[1] | 9.09 |
| Benzyl acetate | 9.09 |
| Romascone ®[2] | 9.09 |
| Citral | 9.09 |
| Ethyl (2E,4Z)-2,4-decadienoate | 9.10 |
| Total | 100 |

[1]Origin: Firmenich SA, Geneva, Switzerland
[2]Methyl 2,2-dimethyl-6-methylene-1-cyclohexanecarboxylate, origin: Firmenich SA, Geneva, Switzerland A perfuming composition according to the invention (Composition A) was prepared by admixing the following ingredients in the amounts indicated.

TABLE 2

Composition A

| Ingredient | Parts (by weight) |
| --- | --- |
| Silwet ® L-7550[1] | 4.5 |
| Water | 10.5 |
| Perfume A | 10.0 |
| Ethanol | 75.0 |
| Total | 100 |

[1]Grafted copolymer of polydimethylsiloxane and poly(propylene glycol), origin: Momentive, Mw = 300 g/mol The polymer was first dissolved at a concentration of 5% wt in a 87.7:12.3 ethanol-water mixture (Solution I). The concentrations of ethanol and of water in Solution (I) were therefore of 83.30% by weight and of 11.75% by weight respectively.

Then, 0.7 g of Perfume A was dissolved in 6.3 g of Solution I. The resulting solution (Solution II) finally contained 75% by weight of ethanol, 10.5% by weight of water, 10% by weight of Perfume A and 4.5% by weight of polymer.

Example 2

Preparation of a Perfuming Composition According to the Invention

A perfuming composition according to the invention (Composition B) was prepared by admixing the following ingredients in the amounts indicated.

TABLE 3

Composition B

| Ingredient | Parts (by weight) |
| --- | --- |
| Aldrich ® 468282[1] | 4.5 |
| Water | 10.5 |
| Perfume A | 10.0 |
| Ethanol | 75.0 |
| Total | 100 |

[1]Poly[dimethylsiloxane-co-methyl(3-hydroxypropyl)siloxane]-graft-tetrakis(1,2-butylene glycol), origin: Sigma-Aldrich, Mw = 560 g/mol Composition B was prepared according to the method described in Example 1.

Example 3

Evaporation Kinetic Measurements of Perfuming Ingredients in a Perfuming Composition According to the Invention An amount of 10 µl of an Eau de Toilette (Composition A) was introduced into each one of 27 GC vials having a capacity of 1.5 ml. The vials were then put into a preheated bain-marie at 30° C.

A reference composition consisting of 10% by weight of Perfume A and 90% by weight of an ethanol-water mixture (9:1), the percentages being relative to the total weight of the composition, was prepared. An amount of 10 µl of this reference composition was introduced into each one of 27 GC vials having a capacity of 1.5 ml. Vials were also put into a preheated bain-marie at 30° C.

After respectively 0, 5, 10, 15, 30, 60, 90, 120 and 240 minutes, there were added to three of the GC vials containing Composition A and to three of the GC vials containing the reference composition 1.5 ml of a solution of isooctane/diethyl ether (9/1 v/v), containing two internal standards, 1,4-dibromobenzene and 4,4'-dibromo-biphenyl, at equal concentration of 150 mg/l, using a Socorex Calibrex 520.

The GC vials were then analyzed on a GC network system 789N and injected by an auto sampler 7683 series from Agilent Technologies. Analyses were carried out using a column HP-5 with a length of 30 m, an inner diameter of 0.25 mm and a film thickness of 0.25 µm. The temperature was set to 100° C. for one minute and was then raised from 100 to 220° C. at a rate of 10° C./minute.

The average amount of remaining perfume present in Composition A and in the reference is represented in FIG. 1 as a function of time. This graph shows that the perfuming composition of the invention comprising a grafted copolymer of polydimethylsiloxane and poly(propylene glycol) and 75% of ethanol had a distinct effect of slowing down the evaporation and increasing the long-lastingness of the perfume it contained. The retention effect increases with time.

Example 4

Evaporation Kinetic Measurements of Perfuming Ingredients in a Perfuming Composition According to the Invention The evaporation of perfuming ingredients in Composition B was measured as described in Example 3.

Figure 2:
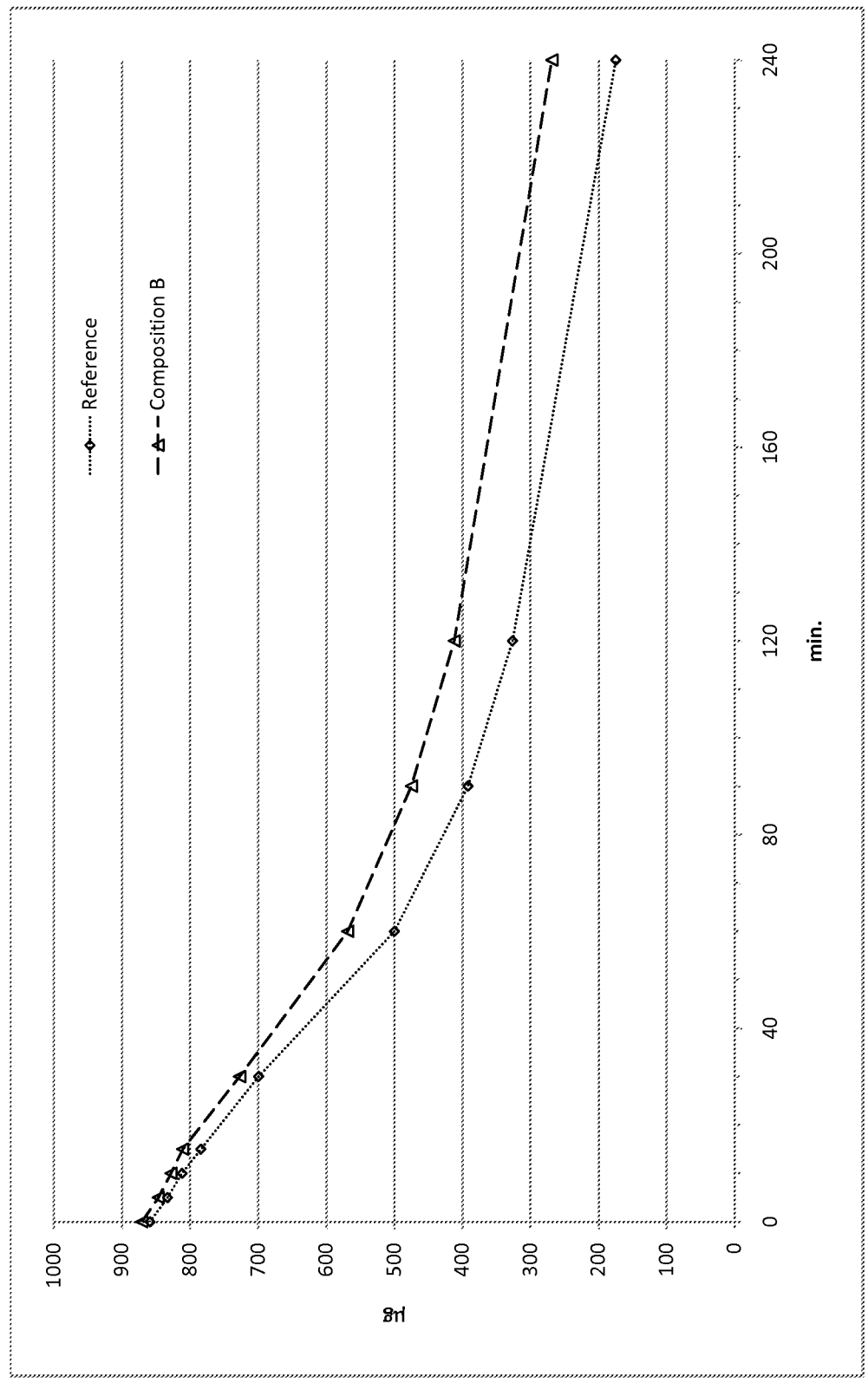
FIG. 2: This graph shows the disappearance of the perfume in Composition B and in the reference as a function of time.

The average amount of remaining perfume present in Composition B and in the reference is represented in FIG. 2 as a function of time. This graph shows that the perfuming composition of the invention comprising poly[dimethylsiloxane-co-methyl(3-hydroxypropyl)siloxane]-graft-tetrakis(1,2-butylene glycol) and 75% of ethanol had a distinct effect of slowing down the evaporation and increasing the long-lastingness of the perfume it contained. The retention effect increases with time.

Example 5

Olfactive Evaluation of a Perfuming Composition According to the Invention

In order to carry out an evaluation of the effect of a composition according to the invention on the perception of the perfuming components over time, two types of samples were prepared:

a) a test sample consisting of Composition A as such
b) a reference sample consisting of 10% by weight of Perfume A and 90% by weight of an ethanol-water mixture (9:1), the percentages being relative to the total weight of the composition.

Panelists were asked to evaluate, on blind tests, the performance of the two samples, by means of smelling strips containing 100 µl of sample. Panelists did four tests at four different times during two sessions. During the first session, they had to test the smell of the strips after a deposition time of 15 minutes and 75 minutes and during the second session they had to test the smell of the strips after a deposition time of 135 minutes and 255 minutes.

The smelling strips were presented to the panel of 36 to 39 people in a blind triangular test. Three smelling strips were showed to the panelists (two identical and one different), the presentation sequence being determined randomly. Each panelist had to determine what sample was differently perceived from the other two. Panellists had to describe their perception and how they determined the difference.

The results of this olfactive evaluation are summarized in the following table.

TABLE 4

Olfactive evaluation of Composition A

| Deposition time (minutes) | Number of panellists | Number of right answers |
| --- | --- | --- |
| 15 | 36 | 20 |
| 75 | 36 | 31 |
| 135 | 39 | 26 |
| 255 | 39 | 37 |

In all cases but after 15 minutes of deposition, panelists found a very significant difference in intensity and perception between the reference and the perfuming composition of the invention during the panel evaluation. The perfuming composition of the invention had a very strong influence on the long-lastingness of the fragrance, in spite of containing high amounts of ethanol, unlike what would have been expected from prior art knowledge. These results confirmed the evaporation kinetic measurements presented in the preceding examples.

Example 6

Olfactive Evaluation of a Perfuming Composition According to the Invention

Composition B was evaluated olfactively as described in Example 5.

The results of this olfactive evaluation are summarized in the following table.

TABLE 5

Olfactive evaluation of Composition B

| Deposition time (minutes) | Panellists number | Number of right answers |
| --- | --- | --- |
| 15 | 37 | 26 |
| 75 | 37 | 36 |
| 135 | 38 | 29 |
| 255 | 38 | 30 |

Panelists found a very significant difference in intensity and perception between the reference and the perfuming composition of the invention, at every step of the panel evaluation. The perfuming compositions of the invention had a very strong influence on the long-lastingness of the fragrance, in spite of containing high amounts of ethanol. This confirmed the results of the evaporation kinetic measurements presented in the preceding examples.

Example 7

Preparation of a Perfuming Composition (Comparative Example)

A perfuming composition (Composition C) was prepared by admixing the following ingredients in the amounts indicated.

TABLE 6

Composition C

| Ingredient | Parts (by weight) |
| --- | --- |
| Dow Corning ® 5329[1] | 4.5 |
| Water | 10.5 |
| Perfume A | 10.0 |
| Ethanol | 75.0 |
| Total | 100 |

[1] Grafted copolymer of polydimethylsiloxane and poly(ethylene glycol), origin: Dow Corning, Mw = 1140 g/mol; amphiphillic organopolysiloxane Composition C was prepared according to the method described in Example 1.

Evaporation Kinetic Measurements of Perfuming Ingredients in Perfume Composition C The evaporation of perfuming ingredients in Composition C was measured as described in Example 3.

Figure 3:
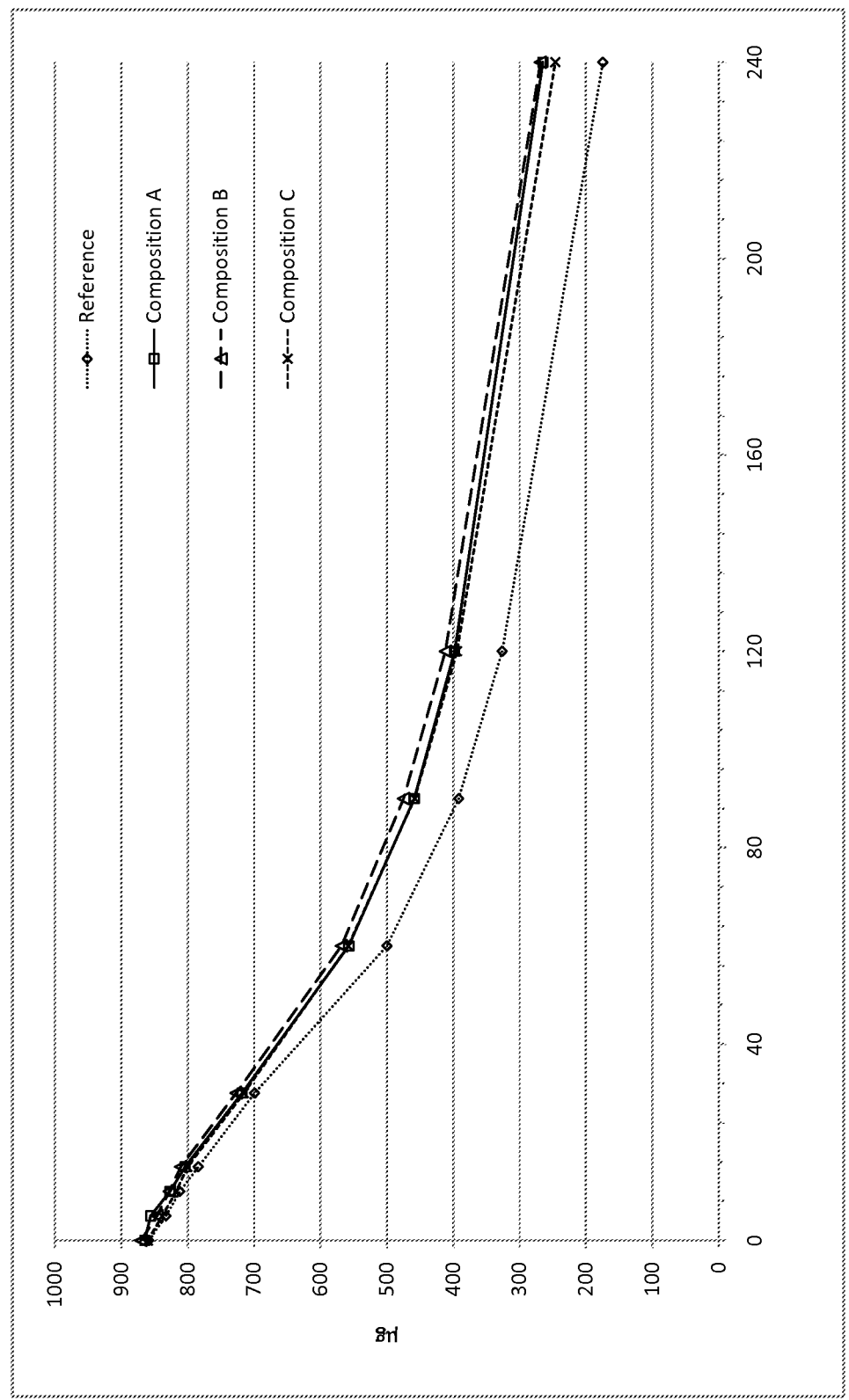
FIG. 3: This graph shows the disappearance of the perfume in Compositions A, B, C and in the reference as a function of time.

The average amount of remaining perfume present in Composition C was compared with the amount of perfume remaining in Compositions A (measured in Example 3), in Composition B (measured in Example 4) and in the reference. The remaining amount of perfume is represented as a function of time in FIG. 3. This graph shows that composition C, which contains an amphiphilic copolymer comprising an hydrophilic part and 75% of ethanol was not able to slow down the evaporation and increase the long-lastingness of the perfuming components it contained with the same efficiency as the Compositions A and B (compositions of the invention). Indeed, the amounts of remaining perfuming ingredients are almost systematically below the remaining amounts of perfuming ingredients in the compositions of the invention. The advantages of the compositions of the invention are even more evident after one hour or more.

Example 8

Preparation of a Perfuming Composition (Comparative Example)

A perfuming composition (Composition D) was prepared by admixing the following ingredients in the amounts indicated.

TABLE 7

Composition D

| Ingredient | Parts (by weight) |
| --- | --- |
| Aldrich ® 457981[1] | 4.5 |
| Water | 10.5 |
| Perfume A | 10.0 |
| Ethanol | 75.0 |
| Total | 100 |

[1] Grafted copolymer of polydimethylsiloxane and poly(ethylene glycol)-co-poly(propylene glycol), origin: Sigma-Aldrich, Mw = 48000 g/mol; amphiphillic organopolysiloxane Composition D was prepared according to the method described in Example 1.

Evaporation Kinetic Measurements of Perfuming Ingredients in Perfume Composition D The evaporation of perfuming ingredients in Composition D was measured as described in Example 3.

Figure 4:
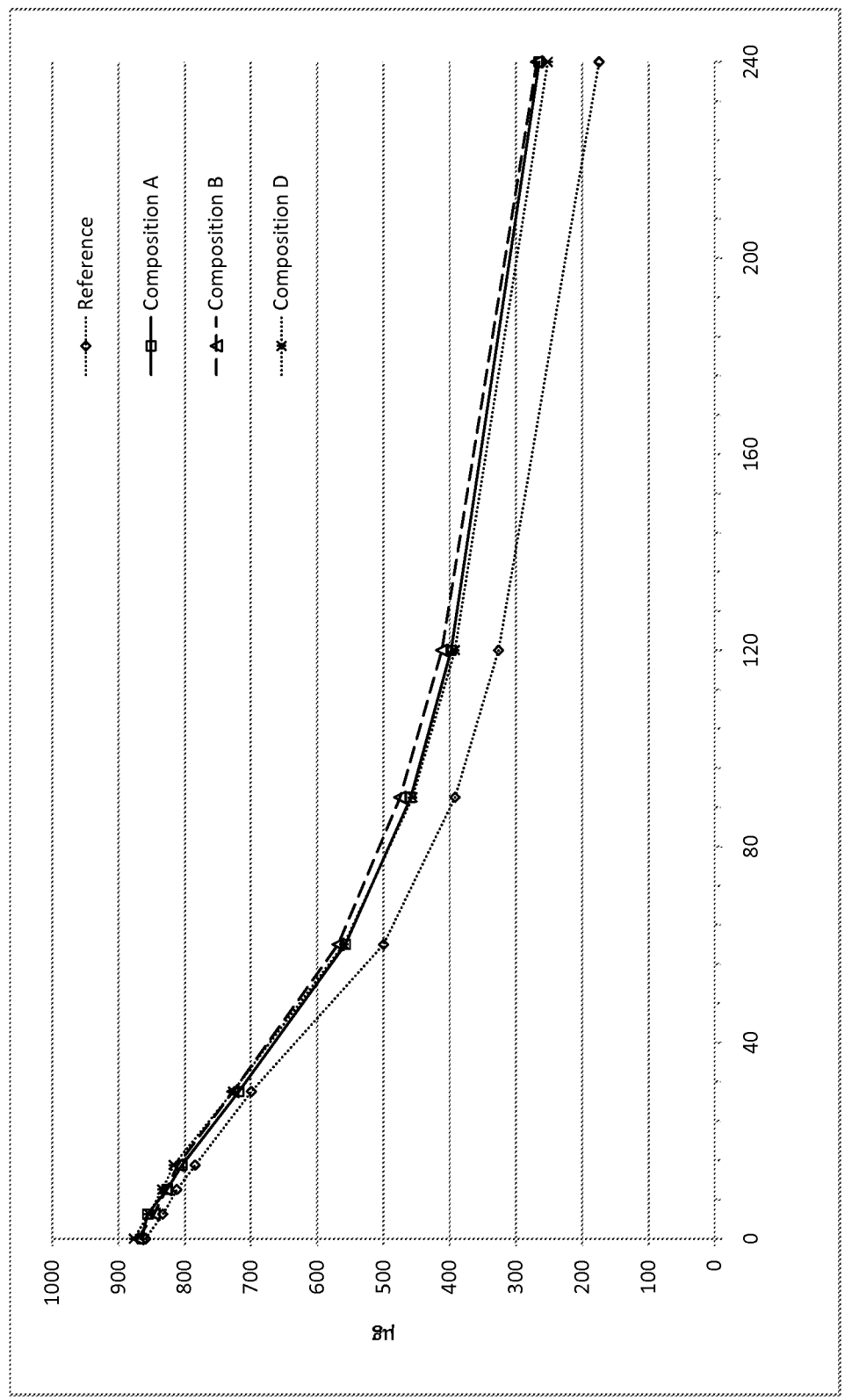
FIG. 4: This graph shows the disappearance of the perfume in Compositions A, B, D and in the reference as a function of time.

The average amount of remaining perfume present in Composition D was compared with the amount of perfume remaining in Compositions A (measured in Example 3), in Composition B (measured in Example 4) and in the reference. The remaining amount of perfume is represented as a function of time in FIG. 4. This graph shows that Composition D, which contains an amphiphilic copolymer comprising an hydrophilic part and 75% of ethanol was not able to slowing down the evaporation and increasing the long-lastingness of the perfuming components it contained with the same efficiency as the Compositions A and B (compositions of the invention). Indeed, the amounts of remaining perfuming ingredients are almost systematically below the remaining amounts of perfuming ingredients in the compositions of the invention. The advantages of the compositions of the invention are even more evident after one hour or more.

Olfactive Evaluation of a Composition D

Composition D was evaluated olfactively as described in Example 5.

The results of this olfactive evaluation are summarized in the following table.

TABLE 8

Olfactive evaluation of Composition D

| Deposition time (minutes) | Panellists number | Number of right answers |
| --- | --- | --- |
| 15 | 39 | 23 |
| 75 | 39 | 21 |
| 135 | 37 | 29 |
| 255 | 37 | 23 |

A limited number of panelists found a very significant difference in intensity and perception between the reference and the perfuming composition of the invention, at every step of the panel evaluation. Panelists were able to distinguish much more easily the test sample consisting of the compositions of the invention (Compositions A and B) than Composition D. The presence of an amphiphilic polymer with high amounts of ethanol in composition E was less efficient to increase the long-lastingness of the fragrance. This confirmed the results of the evaporation kinetic measurements presented in the preceding part of the example.

Example 9

Preparation of an After-Shave Lotion Comprising a Perfuming Composition According to the Invention A perfume was prepared by admixing the following ingredients, in the amounts indicated.

TABLE 9

Perfume B

| Ingredients | Parts (by weight) |
| --- | --- |
| Lilial ®[1] | 7.68 |
| Phenethylol | 7.68 |
| Citronellol | 7.68 |
| Linalool | 7.68 |
| Dihydromyrcenol[2] | 7.68 |
| Florol ®[3] | 7.68 |
| Allyl caproate | 7.69 |
| Allyl heptanoate | 7.68 |
| Benzyl propionate | 7.68 |
| Ethyl propionate | 7.68 |
| Benzyl acetate | 7.83 |
| Hexyl acetate | 7.68 |
| Orange terpenes | 7.68 |
| Total | 100.00 |

[1] 3-(4-tert-butylphenyl)-2-methylpropanal, origin, Givaudan SA, Vernier, Switzerland
[2] Origin: International Flavors & Fragrances, USA
[3] Tetrahydro-2-isobutyl-4-methyl-4(2H)-pyranol, origin: Firmenich SA, Geneva, Switzerland An after-shave lotion (Composition E) comprising a perfuming composition according to the invention was prepared by admixing the following ingredients in the amounts indicated.

TABLE 10

Composition E

| Ingredient | Parts (by weight) |
| --- | --- |
| BHT[1] | 0.05 |
| PEG-60 Hydrogenated Castor oil | 1.99 |
| Ethanol | 54.90 |
| Water | 36.98 |
| Allantoin | 0.1 |
| PEG-8 | 1.99 |
| Perfume B | 3.49 |
| Silwet ® L-7550[2] | 0.50 |
| Total | 100 |

[1] Butylated hydroxytoluene
[2] Grafted copolymer of polydimethylsiloxane and poly(propylene glycol), origin: Momentive, Mw = 300 g/mol BHT, PEG-60 Hydrogenated Castor oil, ethanol, water, allantoin, and PEG-8 were mixed to give a transparent solution. Perfume B (described in example 9) was added to the formulation. Once the perfume was completely dissolved, the copolymer Silwet® L-7550 was dissolved.

Example 10

Evaporation Kinetic Measurements of Perfuming Ingredients from an After-Shave Lotion Comprising a Perfuming Composition According to the Invention Twelve aluminium crucibles were placed on a heating plate at 32° C. An amount of 25 µl of Composition E was introduced with a micropipette in each crucible. After respectively 2, 4, and 8 hours, three of the crucibles were transferred one by one into GC vials previously filled with 1 ml of a solution of 1,4-dibromobenzene (internal standard, 150 mg/l) in isooctane/diethyl ether 9/1 mixture. The solution was then analysed by gas chromatography with an auto-sampler (Agilent 7890A).

The amount of perfume present in Composition E at the beginning of the experiment was also determined by GC. An amount of 25 ml of Composition E was added directly to three GC vials with 1 ml of a solution of 1,4-dibromobenzene (internal standard, 150 mg/l) in isooctane/diethyl ether 9/1 mixture.

The same procedure was repeated with a reference containing the same ingredients as Composition E, except that the polymer Silwet® L-7550 was absent.

Figure 5:
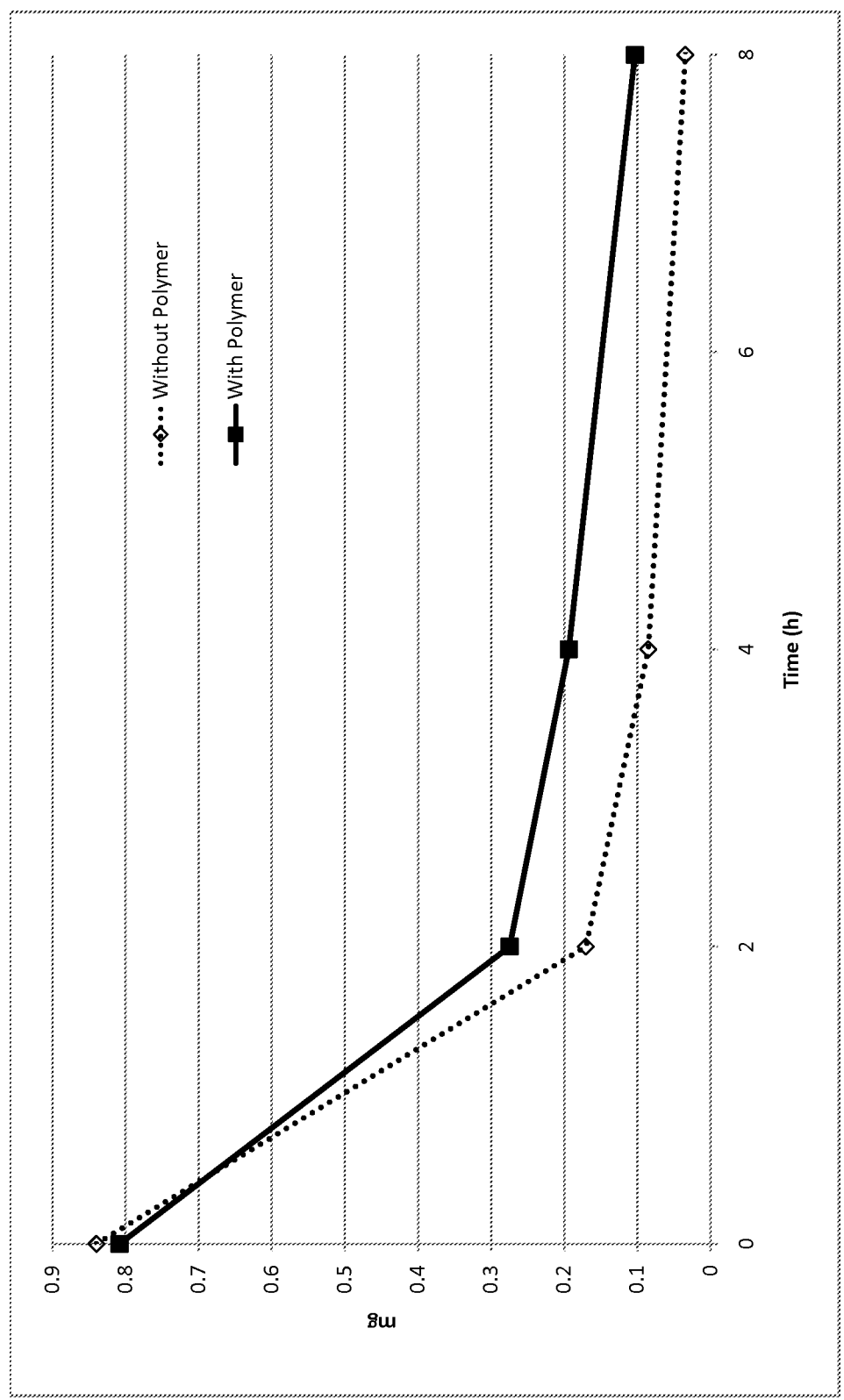
FIG. 5: This graph shows the disappearance of the perfume in Composition E (with polymer) and in the reference (without polymer) as a function of time.

The results are summarized in FIG. 5, which shows the kinetics of the disappearance of the perfume in Composition E compared with the disappearance of the same perfume in the reference. This figure shows that the after-shave lotion of the invention, comprising a grafted copolymer of polydimethylsiloxane and poly(propylene glycol) and 54.9% of ethanol had the distinct effect of slowing down the evaporation of the perfuming components it contained and of increasing the long-lastingness of the perfuming components. After 8 hours, there remained in Composition E 0.103 mg of perfume with 5 different ingredients present, whereas there remained only 0.034 mg of perfume in the reference, with only 4 different ingredients present. The amount of remaining perfume in Composition E was therefore 3 times higher than in the reference.

Example 11

Preparation of a Roll-on Clear Formulation Comprising a Perfuming Composition According to the Invention A roll-on clear formulation (Composition F) was prepared by admixing the following ingredients in the amounts indicated.

TABLE 11

| Composition F | |
| --- | --- |
| Ingredient | Parts (by weight) |
| Aluminium Zirconium pentachlorohydrate | 14.92 |
| PPG-5-ceteth-20 | 1.99 |
| Hydroxyethylcellulose | 0.5 |
| Ethanol | 29.85 |
| Water | 51.24 |
| Perfume B | 1.0 |
| Aldrich ® 468282[1] | 0.50 |
| Total | 100 |

[1] Poly[dimethylsiloxane-co-methyl(3-hydroxypropyl)siloxane]-graft-tetrakis(1,2-butylene glycol), origin: Sigma-Aldrich, Mw = 560 g/mol Composition F was prepared by admixing aluminium-zirconium pentachlorohydrate, PPG-5-ceteth-20, hydroxyethylcellulose, ethanol and water to give a homogenous solution. Perfume B (described in Example 9) was added to the formulation. Once the perfume was completely dissolved, the copolymer Silwet® L-7550 was dissolved.

Example 12

Evaporation Kinetic Measurements of Perfuming Ingredients in a Roll-on Clear Formulation Comprising a Perfuming Composition According to the Invention Kinetic measurements with Composition F were carried out according to the method described in Example 10.

Figure 6:
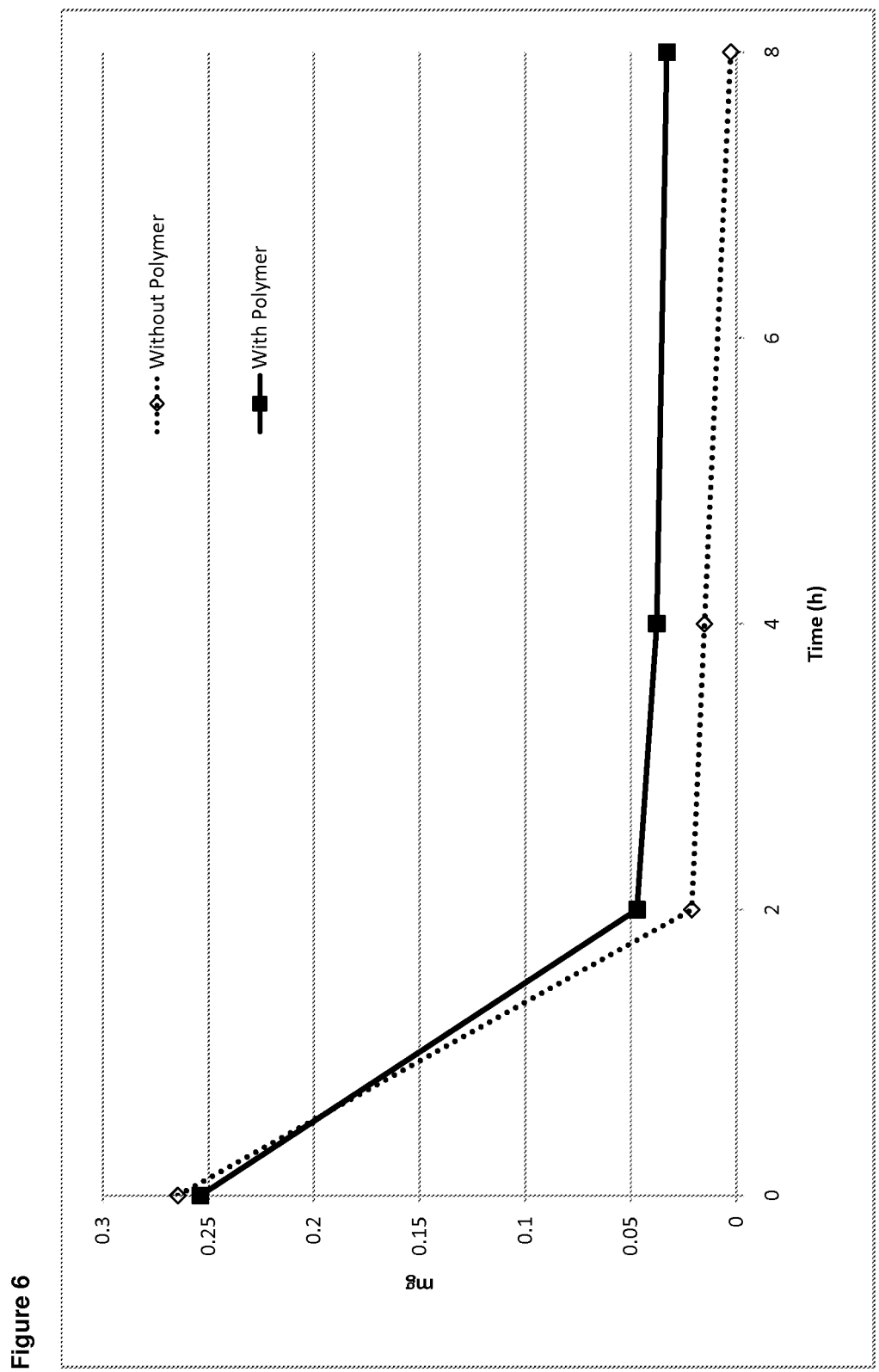
FIG. 6: This graph shows the disappearance of the perfume in Composition F (with polymer) and in the reference (without polymer) as a function of time.

The results are summarized in FIG. 6, which shows that Composition F, comprising a grafted copolymer of polydimethylsiloxane and poly(1,2-butylene glycol) in a roll-on clear formulation had a distinct effect of slowing down the evaporation and increasing the long-lastingness of the perfuming components it contained. There remained 0.033 mg of perfume in Composition F, whereas there remained only 0.003 mg of perfume in the reference. Therefore the remaining amount of perfume was 11 times higher in composition F than in the reference. In addition, after 8 hours, the character of the perfume in Composition F was still very close to the character of the initial perfume. Indeed, 12 perfuming ingredients over the 13 ingredients initially present in Perfume B were still present in Composition F, whereas only Lilial® was detected in the reference.

Example 13

Effect of Different Polymers on the Retention of the Perfume in a Composition According to the Invention A perfume was prepared by admixing the following ingredients, in the amounts indicated.

TABLE 12

| Perfume C | |
| --- | --- |
| Ingredients | Parts (by weight) |
| (Z)-3-hexen-1-ol | 6 |
| Ethyl Acetoacetate | 7.8 |
| Ethyl 2-methyl-pentanoate[1] | 8.64 |
| (Z)-3-hexen-1-ol acetate | 8.52 |
| Limonene | 8.16 |
| Dihydromyrcenol[2] | 9.36 |
| 2,4-Dimethyl-3-cyclohexene-1-carbaldehyde[3] | 8.28 |
| Rose oxyde | 9.24 |
| Benzyl acetate | 9 |
| Ethyl linalool | 20.16 |
| Citral[4] | 18.24 |
| Indole | 7.02 |
| Heliotropine[5] | 9 |
| Methyl anthranilate Dist | 9.06 |
| Eugenol | 9.84 |
| Damascone alpha | 11.52 |
| Coumarine | 8.76 |
| Allyl cyclohexyl propionate | 11.76 |
| Ethyl (2E,4Z)-2,4-decadienoate | 11.76 |
| Lilial ®[6] | 12.24 |
| Total | 204.36 |

[1] Origin: Firmenich SA, Geneva, Switzerland
[2] Origin: International Flavors & Fragrances, USA
[3] Origin: Firmenich SA, Geneva, Switzerland
[4] Origin: Firmenich SA, Geneva, Switzerland
[5] 1,3-Benzodioxole-5-carbaldehyde, origin: Firmenich SA, Geneva, Switzerland
[6] 3-(4-Tert-butylphenyl)-2-methylpropanal, origin: Givaudan SA, Vernier, Switzerland Three perfuming compositions according to the invention (Compositions G, H and I) were prepared by admixing the following ingredients in the amounts indicated in Table 13.

TABLE 13

Compositions G, H and I

| Ingredient | Parts (by weight) |
| --- | --- |
| Ethanol 96° | 79.42 |
| Water | 5.58 |
| Perfume C | 10 |
| Polymer[1)] | 5 |
| Total | 100 |

[1)]In Composition G: Aldrich ® 468282 (poly[dimethylsiloxane-co-methyl(3-hydroxypropyl)siloxane]-graft-tetrakis(1,2-butylene glycol), origin: Sigma-Aldrich, Mw = 560 g/mol)
In Composition H: Silwet ® L-7550 (grafted copolymer of polydimethylsiloxane and poly (propylene glycol), origin: Momentive, Mw = 300 g/mol)
In Composition I: Silwet ® L-7500 (grafted copolymer of polydimethylsiloxane and poly (propylene glycol), origin: Momentive, Mw = 3000 g/mol)

The polymer was first dissolved in a mixture of ethanol and water. Then, the perfume was dissolved in this solution.

The perfume intensity of Compositions G to I and of one control was then evaluated. The control was prepared in the same way as Compositions G to I, except that the polymer was replaced by water.

Compositions G to I and the control were stored during 2 weeks and were then applied separately in an amount of 20 µl on glass slides placed on hot plates heated at 32° C. (skin temperature). After 8 hours at this temperature, the glass slides were presented randomly to a panel of 30 experienced panelists on a blind test basis. The panelists were asked to rate the fragrance intensity of each sample on an unlabelled continuous line scale, where 0 meant no perceptible odor and 10 meant very strong odor.

Figure 7:
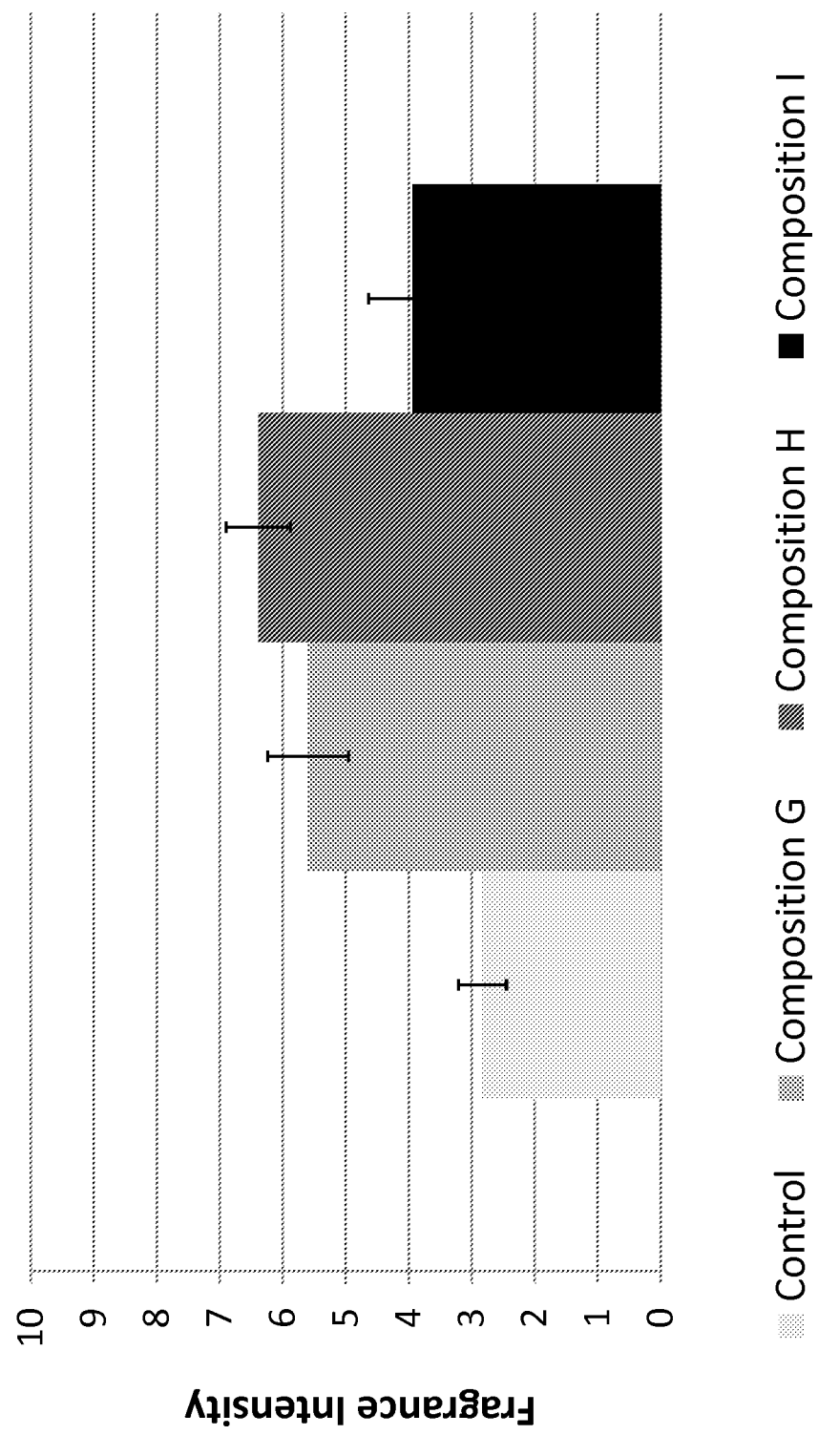
FIG. 7: This graph represents the results of the evaluation of the fragrance intensity in Compositions G, H and I.

The results are summarized in FIG. 7, which shows that the fragrance intensity was perceived more intensely in Compositions G to I than in the control sample. The effect was most evident with Compositions G and H, but an effect was also observed with Composition I, thus indicating that the three polymers mentioned above had the effect of increasing the long-lastingness of the perfume in the compositions of the invention.

Example 14

Compositions According to the Invention Comprising Different Concentrations of Polymer Two perfuming compositions according to the invention (Compositions J and K) were prepared by admixing the following ingredients in the amounts indicated.

TABLE 14

Composition J

| Ingredient | Parts (by weight) |
| --- | --- |
| Ethanol 96° | 79.42 |
| Water | 9.58 |
| Perfume C | 10 |
| Aldrich ® 468282[1)] | 1 |
| Total | 100 |

[1)]Poly[dimethylsiloxane-co-methyl(3-hydroxypropyl)siloxane]-graft-tetrakis(1,2-butylene glycol), origin: Sigma-Aldrich, Mw = 560 g/mol)

TABLE 15

Composition K

| Ingredient | Parts (by weight) |
| --- | --- |
| Ethanol 96° | 79.42 |
| Water | 7.58 |
| Perfume C | 10 |
| Aldrich ® 468282[1)] | 3 |
| Total | 100 |

[1)]Poly[dimethylsiloxane-co-methyl(3-hydroxypropyl)siloxane]-graft-tetrakis(1,2-butylene glycol), origin: Sigma-Aldrich, Mw = 560 g/mol)

The polymer was first dissolved in the mixture of ethanol and water. Then, the perfume was dissolved in this solution.

The perfume intensity of Compositions J, K and of one control was then evaluated. The control was prepared in the same way as Compositions J and K, except that the polymer was replaced by water.

Compositions J, K and the control were stored during 2 weeks and were then applied separately in an amount of 20 µl on glass slides placed on hot plates heated at 32° C. (skin temperature). After 1, 4 and 8 hours, respectively, at this temperature, the glass slides were presented randomly to a panel of 30 experienced panelists on a blind test basis.

Figure 8:
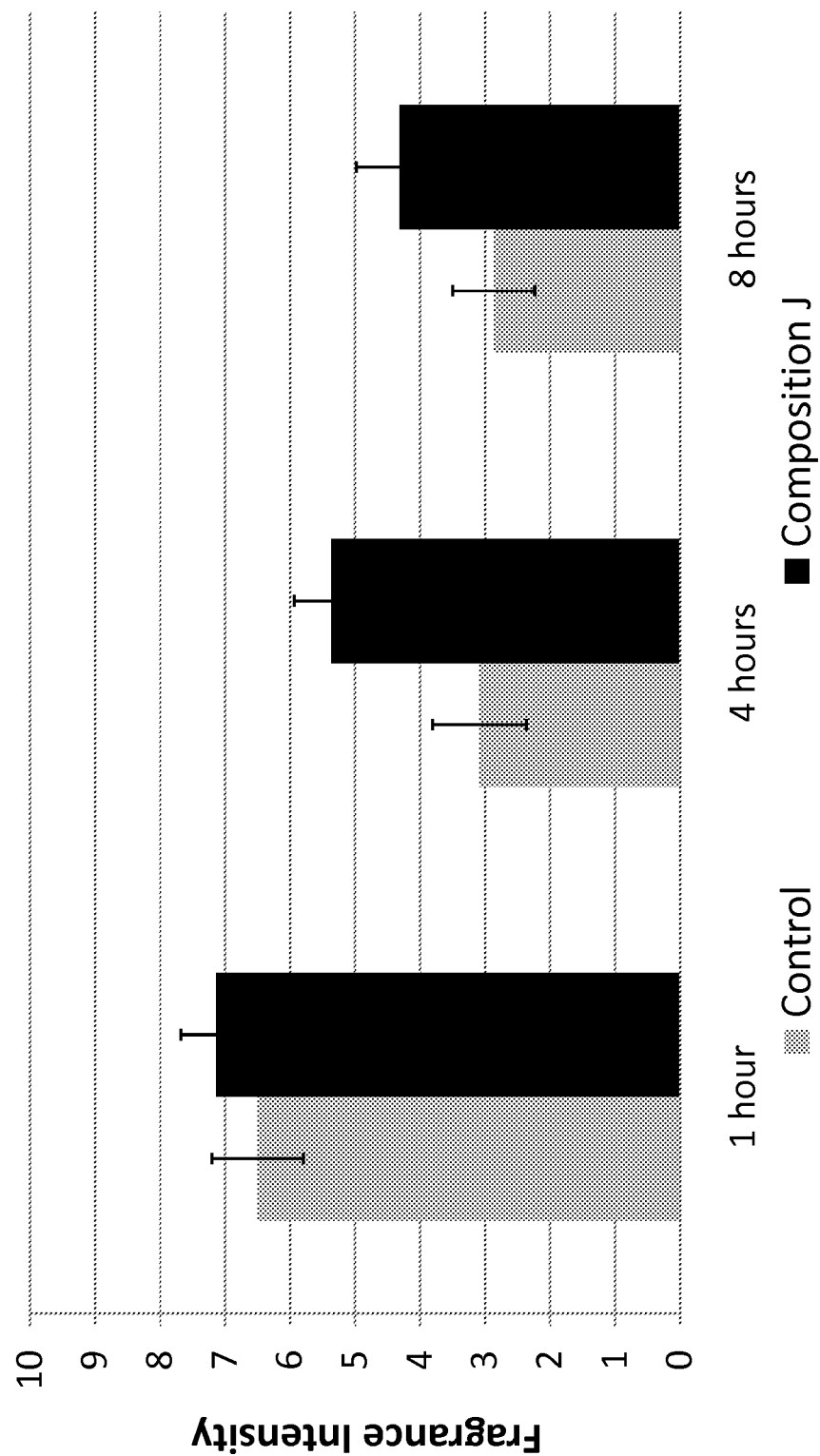
FIG. 8: This graph represents the results of the evaluation of the fragrance intensity of Composition J and of the reference after 1, 4 and 8 hours.

In a first series of tests, the panelists were asked to rate the fragrance intensity of Composition J and of the control on an unlabelled continuous line scale, where 0 meant no perceptible odor and 10 meant very strong odor. The results are summarized in FIG. 8. The perfume is found significantly weaker in the control than in the Composition K (composition of the invention containing 1% of polymer) after 1, 4 and 8 hours, thus showing an improvement of the long-lastingness of the perfume.

Figure 9:
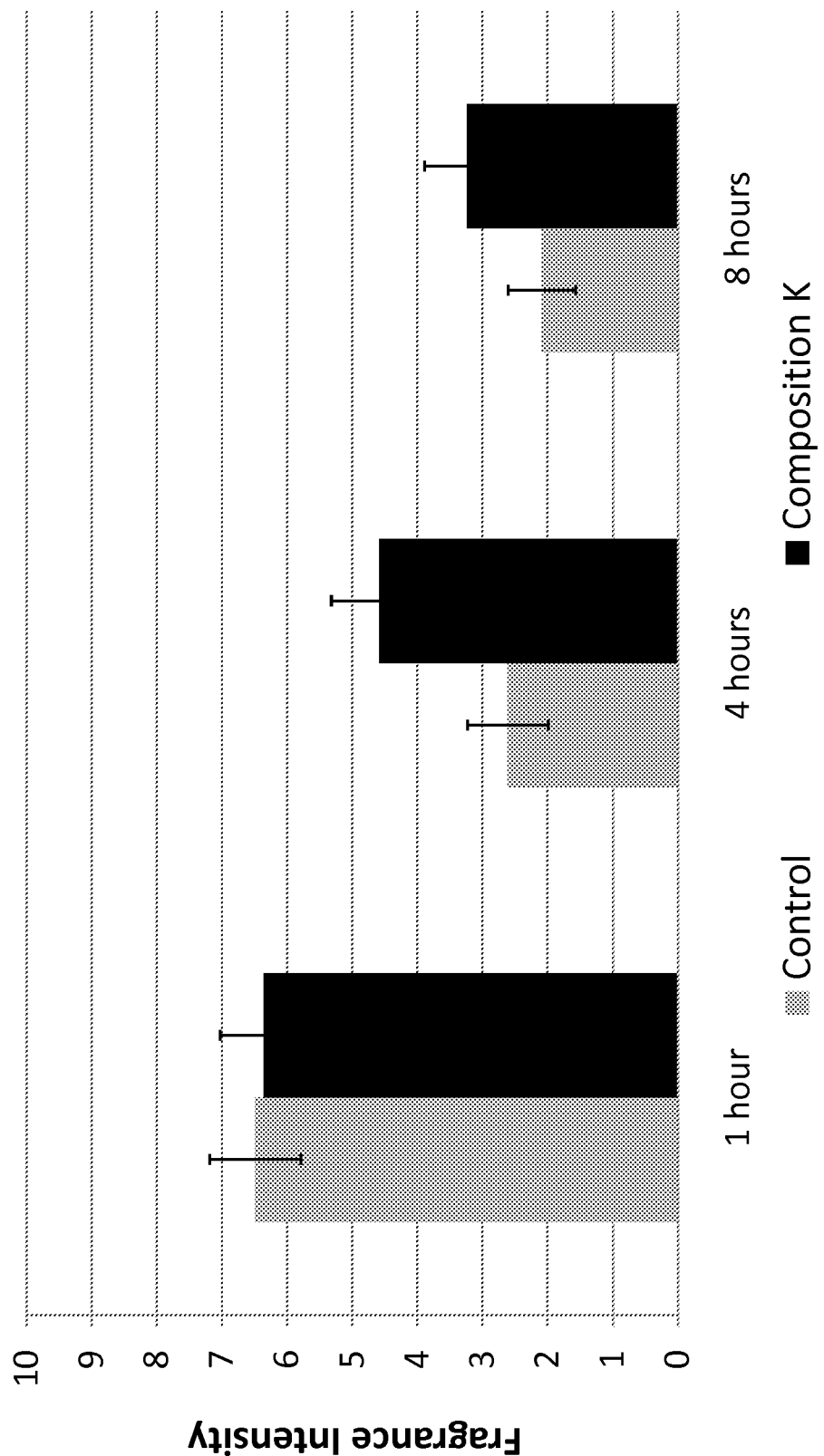
FIG. 9: This graph represents the results of the evaluation of the fragrance intensity of Composition K and of the reference after 1, 4 and 8 hours.

In a second series of tests, the panelists were asked to rate the fragrance intensity of Composition K and of the control on an unlabelled continuous line scale, where 0 meant no perceptible odor and 10 meant very strong odor. The results are summarized in FIG. 9. The perfume is found to have an intensity similar to that of the control after 1 hour, but the perfume is then perceived significantly weaker in the control than in Composition K after 4 and 8 hours. These results also evidence the increase of the long-lastingness of the perfume in Composition K (composition of the invention, with 3% of polymer).

What is claimed is:
1. A perfuming composition comprising
   a) at least one hydrophobic polymeric material which has a grafted structure, is water insoluble and is formed of:
      i) at least one ethanol-compatible block selected from the group consisting of poly (propylene glycol), poly (1,2-butylene glycol) and poly (1,4-butylene glycol);
      ii) poly(dimethylsiloxane) as a core, wherein the at least one ethanol-compatible block is linked to the core and wherein the at least one hydrophobic polymeric material does not include a poly(ethylene glycol) block;
   b) greater than 50% by weight, relative to the total weight of the composition, of ethanol;
   c) water; and
   d) from between 5 and 30% by weight, relative to the total weight of the composition, of at least one perfuming component;
      wherein the hydrophobic polymeric material is present in an amount sufficient to retard evaporation of the perfuming component and increase long lastingness of the perfuming component that is released from the composition.

2. The perfuming composition according to claim 1, wherein:
   a) the at least one hydrophobic polymeric material is present in an amount of from 0.1 to 30%;
   b) the ethanol is present in an amount of no greater than 90%; and
   c) the water is present in an amount of from 5 to 50%;
   with all percentages being defined by weight, relative to the total weight of the perfuming composition.

3. The perfuming composition according to claim 1, wherein the at least one ethanol-compatible block is hydrophobic.

4. The perfuming composition according to claim 1, wherein the hydrophobic polymeric material has a molecular weight between 300 and 100,000 Da or between 300 and 15,000 Da.

5. The perfuming composition according to claim 1, wherein the at least one hydrophobic polymeric material and the at least one perfuming component are present in a weight ratio of between 0.1:10 and 5:10.

6. The perfuming composition according to claim 1, further comprising:
   a) at least one perfume carrier; and
   b) optionally at least one adjuvant.

7. A perfumed article, comprising:
   a) a perfuming composition according to claim 1; and
   b) a consumer product base.

8. The perfumed article according to claim 7, in the form of a perfume, a cologne, an after-shave lotion, a perfumed soap, a shower or bath salt, mousse, cream, oil or gel, a body care product, a hair care product, a deodorant or antiperspirant, a hygiene product, an air freshener or a cosmetic preparation.

9. The perfumed article according to claim 8, in the form of a perfume, a cologne, an after-shave lotion, a perfumed soap, a shower or bath salt, mousse, cream, oil or gel, a body care product, a hair care product, a deodorant or antiperspirant.

10. The perfuming composition according to claim 1, wherein the ethanol is present in an amount of 60 to 90%.

11. The perfuming composition according to claim 1, wherein more than 50% by weight of the at least one hydrophobic polymeric material is at least one ethanol incompatible block so that the hydrophobic polymeric material self-assembles in micelles or vesicles in the composition.

12. A method to confer, enhance, improve or modify the odor properties of a surface, which comprises contacting or treating the surface with a perfuming composition as defined in claim 1.

13. A method to confer, enhance, improve or modify the odor properties of a surface, which comprises contacting or treating the surface with a perfumed article as defined in claim 7.

14. A method for intensifying or prolonging the diffusion effect of a characteristic fragrance of a perfuming compound that is present upon a surface, which comprises treating the surface a perfuming composition according to claim 1 under conditions sufficient to allow release of the perfuming compound over time.

15. A method for intensifying or prolonging the diffusion effect of a characteristic fragrance of a perfuming compound that is present upon a surface, which comprises treating the surface a perfuming composition that includes the perfuming compound according to claim 7 under conditions sufficient to allow release of the perfuming compound over time.

16. A method for increasing long-lastingness of a perfuming component, which comprises preparing a composition as defined in claim 1 using the perfuming component.

* * * * *